(12) United States Patent
Roe et al.

(10) Patent No.: US 6,342,037 B1
(45) Date of Patent: Jan. 29, 2002

(54) DEVICE HAVING FECAL COMPONENT SENSOR

(75) Inventors: Donald C. Roe, West Chester, OH (US); Yury I. Fedosov, Saint Petersburg (RU); Mikhail L. Kruchinin, Saint Petersburg (RU); Oleg N. Khomiakov, Saint Petersburg (RU)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/342,754

(22) Filed: Jun. 29, 1999

Related U.S. Application Data

(63) Continuation-in-part of application No. 09/107,561, filed on Jun. 29, 1998, now Pat. No. 6,149,636, and a continuation-in-part of application No. 09/106,225, filed on Jun. 29, 1998, now Pat. No. 6,186,591.

(60) Provisional application No. 60/131,049, filed on Apr. 26, 1999, and provisional application No. 60/090,993, filed on Jun. 29, 1998.

(51) Int. Cl.⁷ .............................................. G01N 21/78
(52) U.S. Cl. ............................ 600/306; 422/82; 422/1
(58) Field of Search ............................... 600/345–350, 600/306; 422/82.01–82.11

(56) References Cited

U.S. PATENT DOCUMENTS

| | | | |
|---|---|---|---|
| 2,127,538 A | 8/1938 | Seiger | 128/238 |
| 2,926,667 A | 3/1960 | Burger et al. | 128/285 |
| 3,814,101 A | 6/1974 | Kozak | 128/287 |
| 3,881,491 A | 5/1975 | Whyte | 128/287 |
| 3,921,232 A | 11/1975 | Whyte | 5/91 |
| 3,987,792 A | 10/1976 | Hernandez et al. | 128/284 |
| 4,022,211 A | 5/1977 | Timons et al. | 128/287 |
| 4,246,900 A | 1/1981 | Schröder | 128/287 |
| 4,335,722 A | 6/1982 | Jackson | 128/285 |
| 4,356,818 A | 11/1982 | Macias et al. | 128/138 |

(List continued on next page.)

FOREIGN PATENT DOCUMENTS

| | | | |
|---|---|---|---|
| DE | 4 205 894 | 9/1993 | G01N/31/22 |
| EP | 0 560 099 A2 | 9/1993 | B01L/3/00 |
| EP | 0 804 912 | 11/1997 | A61F/13/15 |
| EP | 0 804 913 | 11/1997 | A61F/13/15 |
| EP | 0 804 914 | 11/1997 | A61F/13/15 |
| EP | 0 804 915 | 11/1997 | A61F/13/15 |
| EP | 0 804 916 | 11/1997 | A61F/13/15 |
| EP | 0 804 917 | 11/1997 | A61F/13/15 |
| EP | 0 806 194 | 11/1997 | A61F/13/15 |
| EP | 0 806 195 | 11/1997 | A61F/13/15 |
| EP | 0 815 818 | 1/1998 | A61F/13/15 |
| EP | 0 815 821 | 1/1998 | A61F/13/15 |
| JP | 08122247 | 5/1996 | G01N/21/27 |
| JP | 10-62369 | 3/1998 | G01N/27/00 |
| JP | 10-313894 | 12/1998 | C12Q/1/26 |
| JP | 11-4852 | 1/1999 | A61F/13/42 |
| JP | 01277558 | 11/1999 | A61F/5/44 |
| WO | WO 92/02005 A | 2/1992 | G08F/8/00 |
| WO | WO 94/24974 | 11/1994 | A61F/13/15 |
| WO | WO 96/20681 | 7/1996 | A61F/13/15 |
| WO | WO 97/24150 | 7/1997 | A61L/15/62 |
| WO | WO 97/45082 | 12/1997 | A61F/13/15 |
| WO | WO 97/49989 | 12/1997 | G01N/33/00 |
| WO | WO 98/18505 | 5/1998 | A61L/15/60 |
| WO | WO 98/22063 | 5/1998 | A61F/13/15 |
| WO | WO 98/27417 | 6/1998 | G01N/21/47 |

(List continued on next page.)

Primary Examiner—Robert L. Nasser
(74) Attorney, Agent, or Firm—Jeffrey R. Moore; David M. Weirich; Ken K. Patel

(57) ABSTRACT

The present invention is directed to a device that comprises a sensor adapted to detect one or more specific health and/or nutrition markers in the subject's feces. The device may also signal the caretaker, the subject, or an actuator of the occurrence.

25 Claims, 5 Drawing Sheets

U.S. PATENT DOCUMENTS

| | | | |
|---|---|---|---|
| 4,401,712 A | 8/1983 | Morrison | 428/289 |
| 4,562,043 A * | 12/1985 | Mennen et al. | 422/56 |
| 4,578,359 A | 3/1986 | Oksman et al. | 436/66 |
| 4,636,474 A | 1/1987 | Ogura et al. | 435/291 |
| 4,657,537 A | 4/1987 | Zimmerer | 604/360 |
| 4,681,577 A | 7/1987 | Stern et al. | 604/378 |
| 4,705,050 A | 11/1987 | Markham | 128/749 |
| 4,732,930 A | 3/1988 | Tanaka et al. | 524/742 |
| 4,747,166 A | 5/1988 | Kuntz | 4/144.1 |
| 4,753,645 A | 6/1988 | Johnson | 604/378 |
| 4,754,264 A | 6/1988 | Okada et al. | 340/573 |
| 4,776,331 A | 10/1988 | Simjian | 128/169 |
| 4,778,459 A | 10/1988 | Fuisz | 604/378 |
| 4,787,896 A | 11/1988 | Houghton et al. | 604/385.1 |
| 4,790,836 A | 12/1988 | Brecher | 604/359 |
| 4,796,014 A | 1/1989 | Chia | 340/573 |
| 4,842,593 A | 6/1989 | Jordan et al. | 604/360 |
| 4,981,465 A | 1/1991 | Ballan et al. | 600/32 |
| 5,002,541 A | 3/1991 | Conkling et al. | 604/319 |
| 5,100,933 A | 3/1992 | Tanaka et al. | 523/300 |
| 5,118,607 A | 6/1992 | Bignami et al. | 435/7.1 |
| 5,181,905 A | 1/1993 | Flam | 602/41 |
| 5,220,919 A | 6/1993 | Phillips et al. | 128/632 |
| 5,264,830 A | 11/1993 | Kline et al. | 340/604 |
| 5,330,459 A | 7/1994 | Lavon et al. | 604/385.1 |
| 5,341,127 A | 8/1994 | Smith | 340/604 |
| 5,342,343 A | 8/1994 | Kitaoka et al. | 604/385.2 |
| 5,416,469 A | 5/1995 | Colling | 340/573 |
| 5,468,236 A | 11/1995 | Everhart et al. | 604/361 |
| 5,468,366 A | 11/1995 | Wegner et al. | 204/403 |
| 5,520,674 A | 5/1996 | Lavon et al. | 604/385.1 |
| 5,558,655 A | 9/1996 | Jezzi et al. | 604/378 |
| 5,568,128 A | 10/1996 | Nair | 340/604 |
| 5,582,604 A | 12/1996 | Ahr et al. | 604/385.1 |
| 5,607,417 A | 3/1997 | Batich et al. | 604/890.1 |
| 5,609,590 A | 3/1997 | Herbig et al. | 604/892.1 |
| 5,641,562 A | 6/1997 | Larson et al. | 442/394 |
| 5,643,241 A | 7/1997 | Ahr et al. | 604/385.1 |
| 5,649,914 A | 7/1997 | Glaug et al. | 604/361 |
| 5,653,862 A | 8/1997 | Parris | 205/777.5 |
| 5,658,268 A | 8/1997 | Johns et al. | 604/361 |
| 5,678,564 A | 10/1997 | Lawrence et al. | 128/761 |
| 5,681,298 A | 10/1997 | Brunner et al. | 604/361 |
| 5,694,932 A * | 12/1997 | Michel | 600/345 |
| 5,702,376 A | 12/1997 | Glaug et al. | 604/361 |
| 5,728,125 A | 3/1998 | Salinas | 604/361 |
| 5,733,272 A | 3/1998 | Brunner et al. | 604/359 |
| 5,736,590 A | 4/1998 | Rasmussen | 523/113 |
| 5,759,866 A * | 6/1998 | Machida et al. | 436/518 |
| 5,760,694 A | 6/1998 | Nissim et al. | 340/604 |
| 5,769,834 A | 6/1998 | Reiter et al. | 604/385.1 |
| 5,770,528 A | 6/1998 | Mumick et al. | 422/59 |
| 5,780,239 A * | 7/1998 | Carter et al. | 435/7.1 |
| 5,790,036 A | 8/1998 | Fisher et al. | 340/605 |
| 5,792,049 A * | 8/1998 | Eppstein et al. | 600/306 |
| 5,797,892 A | 8/1998 | Glaug et al. | 604/361 |
| 5,840,584 A | 11/1998 | Waldenburg | 436/66 |
| 5,876,393 A | 3/1999 | Ahr et al. | 604/387 |
| 5,885,264 A | 3/1999 | Matsushita | 604/361 |
| 5,922,544 A | 7/1999 | Miyai et al. | 435/6 |
| 6,108,570 A * | 8/2000 | Kohen et al. | 600/345 |
| 6,171,238 B1 * | 1/2001 | Klimes et al. | 600/345 |
| 6,203,496 B1 | 3/2001 | Gael et al. | |

FOREIGN PATENT DOCUMENTS

| | | | |
|---|---|---|---|
| WO | WO 98/29079 | 7/1998 | A61F/13/15 |
| WO | WO 99/02985 | 1/1999 | G01N/31/22 |
| WO | WO 99/07317 | 2/1999 | A61F/13/15 |
| WO | WO 99/31486 | 6/1999 | G01N/21/47 |
| WO | WO 99/51179 | 10/1999 | A61F/13/42 |

* cited by examiner

DEVICE HAVING FECAL COMPONENT SENSOR

This application is a non-provisional filing of prior provisional Application Serial No. 60/131,049, filed on Apr. 26, 1999, and a continuation-in-part of application Ser. No. 09/107,561, now U.S. Pat. No. 6,149,636, filed on Jun. 29, 1998, Ser. No. 09/106,225, filed on Jun. 29, 1998, now U.S. Pat. No. 6,186,591, and Ser. No. 60/090,993, filed on Jun. 29, 1998.

FIELD OF THE INVENTION

The present invention relates to devices having sensors adapted to detect and/or measure components of feces useful as health and/or nutritional indicators.

BACKGROUND OF THE INVENTION

Today, devices comprising sensors to detect various disease or health conditions of individuals by analyzing blood for health markers are known. The most widely known include blood glucose monitors that allow patients with diabetes to monitor their blood glucose levels and determine the amount of insulin required to balance their sugar levels. Additionally, portable devices with sensors adapted to detect alcohol (i.e., ethanol) levels in the exhaled breath of suspected intoxicated drivers are widely known and employed by various law enforcement agencies. These devices have generally replaced traditional laboratory testing as the preferred means for these applications because of their convenience and reliability. The devices respond to pre-defined target analytes in the blood and exhaled breath and provide an indication of the presence and/or level of the target analyte. However, none of these specifically detect chemical and/or biological components of the subject's feces that function as markers for potential health issues and/or nutritional status. No convenient, accurate means are available to caregivers and/or medical personnel to quickly provide data on fecal health and/or nutritional markers, especially those associated with diarrheal disease, poisoning, and malnutrition. Additionally, the devices do not predict when a health or nutrition-related event is about to occur and signal subject or caregiver that prophylactic or remedial action is required prior to the onset of clinically observable symptoms.

SUMMARY OF THE INVENTION

The present invention is directed to a device that comprises a sensor adapted to detect one or more specific health and/or nutrition markers in feces. The device may also signal the caretaker of the occurrence or quantity of the marker.

DETAILED DESCRIPTION OF THE INVENTION

Figure 1:
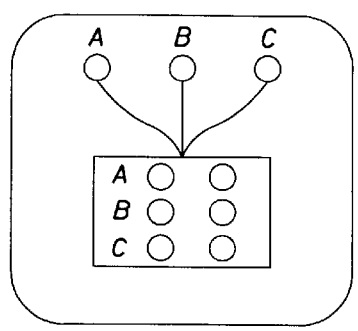
FIG. 1 is a plan view of a device made in accordance with the present invention adapted to be temporarily affixed to a subject's skin or a durable or disposable subject device, the device having sensors adapted to detect three different analytes and an indicator adapted to provide an indication of the presence of each analyte.

As used herein, the term "device" refers to devices or appliances which analyze bodily waste, particularly feces, for target chemical and/or biological analytes useful as health and/or nutritional markers. The device is generally reusable. The term "reusable" is used herein to describe devices which have at least one component which is not discarded immediately following its initial use, but which is employed in subsequent uses of the device. At least a portion of the device may be disposable. The term "disposable" is used herein to describe absorbent devices which generally are not intended to be laundered or otherwise restored or reused (i.e., they are intended to be discarded after a single use).

The device 20 preferably also includes at least one sensor 60 adapted to detect one or more health and/or nutritional markers in bodily waste and having the capability to provide a signal of said detection to the subject, caretaker, or an actuator. The term "subject", as used herein, refers to a human whose waste is to be analyzed. The term "caretaker", as used herein, refers to an individual responsible for the care of the subject, such as a nurse or a parent. The term "medical personnel", as used herein, refers to individuals trained in a medically related field, such as doctors, nurses, and lab technicians. In certain instances, these terms may be used interchangeably. For example, the subject may also be the caregiver, the caregiver may be a medical professional, etc. As used herein, the term "sensor" refers to a device that is capable of detecting an event or a parameter that is associated with an event. A parameter associated with an event is any measurable signal that correlates with the occurrence of an event within the frame of reference of the system (i.e., a signal caused by the waste, the subject, or a component thereof). Sensors include anything that responds to one or more specific inputs. Sensors may be chemical, electrochemical, biochemical, or biological. The devices of the present invention specifically comprise sensors that provide a signal to the subject, caretaker and/or medical personnel indicating the presence and/or concentration of one or more health or nutritional markers in bodily waste such as feces, urine or menses. The signal may be an optical signal, including visual signals (e.g., a colorimetric or flourescent indicator), chemical signal (e.g., a change in pH, enzyme activity, or concentration of any other chemical species), or an electrical signal.

"Health markers" and "nutritional markers" (e.g., in human feces), as used herein, refer to any elemental, chemical, or biological components that may be found in the waste, and any combinations of or relationships between (e.g., ratios, etc.) the components, having a defined relationship with the individual's health (e.g., disease, infection, poisoning, etc.) and nutritional status, respectively. The nutritional status of the subject includes, for example, metabolic efficiency, nutrient deficiencies, nutrient absorption or malabsorption, food and drink intake, food allergies (e.g., to peanuts), food intolerance (e.g., lactose intolerance), colonic bacteria ecology (e.g., beneficial bacteria such as bifidobacteria and lactobacillus), and total energy balance.

Health markers may include heavy metals (e.g., lead, mercury, etc.), radioactive substances (e.g., cesium, strontium, uranium, etc.), fats, enzymes, endogenous secretions, proteinaceous matter (e.g., casts), mucous, and microorganisms (described in more detail hereinafter in the biosensor section) that may be related to various health issues such as infection, diarrhea, gastrointestinal distress or disease, or poisoning. Heavy metals, especially in certain developing countries and in older and/or less affluent areas of developed countries, are a serious health risk. For example, lead and mercury poisoning may occur upon the ingestion of these heavy metals from environmental sources (e.g., from lead paint, unregulated heavy industries, etc.) and can be fatal. More commonly, low-level poisoning by these and other heavy metals results in retarded intellectual and/or physical development, especially in children, that may occur over a long time and have lasting effects on the individual. Proteinaceous masses, such as casts (e.g., in urine) may be sensed by targeting Tamm-Horsfall protein. A suitable example of a sensor for Tamm-Horsfall protein is described in U.S. Pat. No. 5,780,239, which is incorporated herein by reference. Suitable sensors for heavy metals, and/or the discriminating means useful for the sensors, are described more detail in U.S. Pat. Nos. 5,595,635; 5,865,972; 5,814,205; 5,468,366, all of which are incorporated herein by reference.

Non-limiting examples of nutritional markers include calcium, vitamins (e.g., thiamine, riboflavin, niacin, biotin, folic acid, pantothenic acid, ascorbic acid, vitamin E, etc.), electrolytes (e.g., sodium, potassium, chlorine, bicarbonate, etc.), fats, fatty acids (long and short chain), soaps (e.g., calcium palmitate), amino acids, enzymes (e.g., lactose, amylase, lipase, trypsin, etc.), bile acids and salts thereof, steroids, and carbohydrates. For example, calcium malabsorption is important in that it may lead to a long-term bone-mass deficiency. While the importance of calcium absorption in adults, particularly older women, is much publicized, it is also an important consideration in children (especially infants). Infant diet may impact calcium absorption and, therefore, bone mass and/or density. It has been shown, for example, that changing the position of palmitic acid on triglycerides in infant formula from the 2-position (i.e., like human breast-milk) to the 1- and/or 3-position (e.g., as in some infant formulas), results in less cleavage of the palmitic acid from the triglyceride "backbone", and therefore absorption, of this nutrient by the body. The uncleaved palmitic acid binds calcium in the digestive tract as a soap (i.e., calcium palmitate) and leaves the body in the feces. (This process is described in more detail in *Archive of Disease in Childhood* (November 1997) 77 F178–F184.) Therefore, the calcium and/or soap content in feces is one potential means of assessing calcium absorption by the digestive system. Suitable colorimetric calcium sensors based on Arsenazo III (acidic environment) and Cresolphthalein Complexone (basic environment) are available from Sigma-Aldrich Chemical of St. Lois, Mo. as catalog numbers 588-3 and 587-A, respectively. Other exemplary sensors for calcium, and/or the discriminating means useful for the sensors, are described more detail in U.S. Pat. Nos.5,705,620; 5,580,441; and 5,496,522, all of which are incorporated herein by reference.

The sensors of the present invention may be associated with a carrier structure. The carrier structure may hold, stabilize, and/or at least partially encapsulate the sensor. Examples of carrier structures include one or more layers of elastic or inelastic woven and nonwoven webs, films, foams, scrims, hydrogels, and the like. The sensor may be attached to the carrier structure, held between two or more components, layers, or folds of the carrier structure, or may be sealed within the carrier structure. The carrier structure may optionally comprise an adhesive or skin adhering composition or other attachment means to secure at least a portion of said carrier structure to the device or a component thereof or to the subject's skin. Further, at least a portion of the carrier may be water soluble.

In certain embodiments of the present invention, the sensor 60 may comprise a biosensor. As used herein, the term "biosensor" is defined as a component comprising one or more biologically reactive means being adapted to detect one or more target pathogenic microorganisms or related biomolecules (e.g., an enzyme sensor, organella sensor, tissue sensor, microorganism sensor, immunosensor or electrochemical sensor), The term "biologically reactive" is defined as having the capability to selectively interact with, and preferably bind, target pathogenic microorganisms and/or related biomolecules as described herein. Generally, biosensors function by providing a means of specifically binding, and therefore detecting, a target biologically active analyte. In this way, the biosensor is highly selective, even when presented with a mixture of many chemical and biological entities, such as feces. Often the target biological analyte is a minor component of a complex mixture comprising a multiplicity of biological and other components. Thus, in many biosensor applications, detection of target analytes to the parts-per-billion, parts-per-trillion, or even lower levels is necessary. Accordingly, discrimination ratios of about $10^7$-$10^8$ or greater may be required for the biosensor to recognize the target biological analyte in a complex mixture.

The biosensor of the present invention may comprise a bio-recognition element, or molecular recognition element, that provides the highly specific binding or detection selectivity for a particular analyte. The bio-recognition element, or system, may be a biologically derived material such as an enzyme or sequence of enzymes; an antibody; a membrane receptor protein; DNA; an organelle, a natural or synthetic cell membrane; an intact or partial viable or nonviable bacterial, plant or animal cell; or a piece of plant or mammalian tissues, and generally functions to interact specifically with a target biological analyte. The bio-recognition element is responsible for the selective recognition of the analyte and the physico-chemical signal that provides the basis for the output signal.

Biosensors may include biocatalytic biosensors, and bio-affinity biosensors. In biocatalytic biosensor embodiments, the bio-recognition element is "biocatalytic" and may comprise an enzyme, organelle, piece of plant or mammalian tissue, or whole cells, the selective binding sites "turn over" (i.e., can be used again during the detection process), resulting in a significant amplification of the input signal. Biocatalytic sensors such as these are generally useful for real-time, continuous sensing.

Bioaffinity sensors are generally applicable to bacteria, viruses, and toxins and include chemoreceptor-based biosensors and/or immunological sensors (i.e. immunosensors). Chemoreceptors are complex biomolecular macroassemblies responsible, in part, for a viable organism's ability to sense chemicals in its environment with high selectivity. Chemoreceptor-based biosensors comprise one or more natural or synthetic chemoreceptors associated with a means to provide a signal (visual, electrical, etc.) of the presence or concentration of a target biological analyte. In certain embodiments, the chemoreceptor may be associated with an electrode (i.e., an electrical transducer) so as to provide a detectable electrical signal. Chemoreceptors may include whole or partial nerve bundles (e.g., from antennae or other sensing organs) and/or whole or partial natural or synthetic cell membranes. On the other hand, the bio-recognition elements of immunosensors are generally antibodies. Antibodies are highly specific and can be made toward bacteria, viruses, fragments of microorganisms (e.g., bacterial cell walls, parasite eggs or portions thereof, etc.), and large biomolecules. Suitable antibodies may be monoclonal or polyclonal. In any case, bioaffinity biosensors are generally irreversible because the receptor sites of the biosensor become saturated when exposed to the target biological analyte.

In certain embodiments, biocatalytic bioaffinity biosensors may be combined, such as RNA/DNA probes or other high-affinity binding systems wherein the initial bio-recognition event is followed by biological amplification of the signal. For example, a specific bacteria may be detected by a biosensor comprising genetic material, such as DNA, as a bio-recognition element and PCR (i.e., polymerase chain reaction) amplification to detect small numbers (e.g., less than or equal to 500) organisms. Biocatalytic and bioaffinity biosensor systems are described in more detail in *Journal of Chromatography*, 510 (1990) 347–354 and in the *Kirk-Othmer Encyclopedia of Chemical Technology*, $4^{th}$ ed. (1992), John Wiley & Sons, NY, the disclosure of which is incorporated by reference herein.

The biosensors of the present invention preferably detect biologically active analytes related to impending (i.e., future presentation of symptoms is likely) or current human systemic disease states, including, but not limited to, pathogenic bacteria, parasites (e.g., any stage of the life cycle, including eggs or portions thereof, cysts, or mature organisms), viruses, fungi such as *Candida albicans*, antibodies to pathogens, and/or microbially produced toxins. Additionally, the biosensor may target biologically active analytes related to impending or current localized health issues, such as stress proteins (e.g., cytokines) and IL-1α (interleukin 1-alpha) that may precede the clinical presentation of skin irritation or inflammation. In preferred embodiments, the biosensor functions as a proactive sensor, detecting and signaling the subject, a caretaker or medical personnel of the impending condition prior to the presentation of clinical symptoms. This allows time to administer prophylactic or remedial treatments to the subject which can significantly reduce, if not prevent, the severity and duration of the symptoms. Further, the sensor 60, by detecting the presence of a target biological analyte in the subject's bodily waste (e.g., feces), may detect residual contamination on a surface, such as skin or environmental surface, in contact with the biosensor, and provide and appropriate signal.

The physico-chemical signal generated by the bio-recognition element or elements may be communicated visually to the caretaker or medical personnel (i.e., via a color change visible to the human eye). Other embodiments may produce optical signals, which may require other instrumentation to enhance the signal. These include flourescence, bioluminesence, total internal reflectance resonance, surface plasmon resonance, Raman methods and other laser-based methods, such as LED or laser diode sensors. For example, exemplary surface plasmon resonance biosensors are available as IBIS I and IBIS II from XanTec Analysensysteme of Muenster, Germany, which may comprise bioconjugate surfaces as bio-recognition elements. Alternatively, the signal may be processed via an associated transducer which, for example, may produce an electrical signal (e.g., current, potential, inductance, or impedance) that may be displayed (e.g., on a readout such as an LED or LCD display) or which triggers an audible or tactile (e.g., vibration) signal or which may trigger an actuator, as described herein. The signal may be qualitative (e.g., indicating the presence of the target biological analyte) or quantitative (i.e., a measurement of the amount or concentration of the target biological analyte). In such embodiments, the transducer may optionally produce an optical, thermal or acoustic signal.

In any case, the signal may also be durable (i.e., stable and readable over a length of time typically at least of the same magnitude as the usage life of the device) or transient (i.e., registering a real-time measurement). Additionally, the signal may be transmitted to a remote indicator site (e.g., via a wire, or transmitter, such as an infrared or rf transmitter) including other locations within or on the device or remote devices. Further, the sensor 60, or any of its components, may be adapted to detect and/or signal only concentrations of the target biological analyte above a predefined threshold level (e.g., in cases wherein the target biological analyte is normally present in the bodily waste or when the concentration of the analyte is below a known "danger" level).

As described above, the target analytes that the biosensors of the present invention are adapted to detect may be pathogenic microorganisms such as the pathogenic microorganisms implicated in human gastrointestinal diseases, especially those resulting in diarrhea. This type of pathogen is particularly important to monitor due to the number of children who become seriously ill or die each year from diarrheal diseases. It has been found that severe chronic diarrhea may result in weight loss and permanent physical and mental developmental retardation. A non-limiting list of pathogenic bacteria that the sensor 60 may detect include any of the various pathogenic strains of Escherichia coli (commonly known as *E. coli*); Salmonella strains, including *S. typhi, S. paratyphi, S. enteridiis, S. typhimurium*, and *S. heidelberg*; Shigella strains such as *Shigella sonnei, Shigella flexneri, Shigella boydii*, and *Shigella dysenteriae; Vibrio cholerae; Mycobacterium tuberculosis; Yersinia enterocolitica; Aeromonas hydrophila; Plesiomonas shigelloides*; Campylobacter strains such as *C. jejuni* and *C. coli; Bacteroides fragilis*; and Clostridia strains, including *C. septicum, C. perfringens, C. botulinum*, and *C. difficile*. A non-limiting example of a commercially available biosensor adapted to detect *E. coli* is available from AndCare, Inc. of Durham, N.C. as test kit #4001. As another non-limiting example, ABTECH, Scientific, Inc., of Yardley, Pa. offers "bioanalytical biotransducers", available as BB Au-1050.5-FD-X, which may be rendered biospecific (for microorganisms or other target biological analytes as described herein) by covalently immobilizing polypeptides, enzymes, antibodies, or DNA fragments to their surfaces. Other suitable microbial biosensors are described in U.S. Pat. No. 5,869,272 (gram negative organisms); U.S. Pat. No. 5,795,717 (Shigella); U.S. Pat. Nos. 5,830,341; 5,795,453; 5,354,661; 5,783,399; 5,840,488; 5,827,651; 5,723,330; and 5,496,700, all of which are incorporated herein by reference.

The target analytes that the biosensors of the present invention are adapted to detect may also be viruses. These may include diarrhea-inducing viruses such as rotavirus, or other viruses such as rhinovirus and human immunodeficiency virus (HIV). An exemplary biosensor adapted to detect HIV is described in U.S. Pat. Nos. 5,830,341 and 5,795,453, referenced above. The disclosure of each of these patents is incorporated by reference herein.

In alternative embodiments, the target analytes that the biosensors of the present invention are adapted to detect may also be parasites, especially those which inhabit the gastrointestinal tract during some point in their life-cycle. Such parasites may include protozoans, worms, and other gastrointestinal parasites. Other examples of parasites which may be detected include *entamoeba histolytica* (which cause amoebic dysentery), *trypana cruzi* (which causes Chagas disease), and *plasmodium falciparum*.

In yet other embodiments, the target analytes the biosensors of the present invention are adapted to detect may fungi such as *Candida albicans*. In addition to pathogenic bacteria, certain beneficial colonic bacteria may be detected and/or measured as a health indicator, such as Bifidobacteria and Lactobacillus strains.

The target analytes that the biosensors of the present invention are adapted to detect may also be proteins or antigens related to skin distress. Preferably, these analytes are detectable on or at the skin surface, preferably prior to the presentation of clinically observable skin irritation. These may include stress proteins such as cytokines, histamine, and other immune response factors including interleukins (such as IL-1α, WL-2, IL-3, IL-4, and IL-8) and interferons (including interferons a and g). Again, these are preferably detectable by the sensor 60 prior to the onset of clinically observable redness, irritation, or dermatitis. Additionally, the biosensors of the present invention may be adapted to detect enzymes, or other biological factors, implicated in skin irritation (e.g., diaper dermatitis), including tryspin, chymotrypsin, and lipase.

The biosensors of the present invention may also comprise bio-recognition systems, including enzymes or binding proteins such as antibodies immobilized onto the surface of physico-chemical transducers. For example, a specific strain of bacteria may be detected via biosensors employing antibodies raised against that bacterial strain. Alternatively, a target bacteria may be detected by a bio-recognition element (including antibodies and synthetic or natural molecular receptors) specific to extracellular products of the target bacteria, such as toxins produced by that strain (e.g., E. coli). Exemplary enzyme electrodes that may be used to detect phenols (e.g. in urine or feces) include tyrosinase based electrodes or polyphenol oxidase enzyme electrodes described in U.S. Pat. No. 5,676,820 entitled "Remote Electrochemical Sensor," issued to Joseph Wang et al. on Oct. 14, 1997 and U.S. Pat. No. 5,091,299 entitled "An Enzyme Electrode For Use In Organic Solvents," issued to Anthony P. F. Turner et al. on Feb. 25, 1992, respectively. Both of these patents are incorporated by reference herein.

In any of the foregoing examples, the specific microorganism may be directly detected or may be detected by binding a toxin, enzyme, or other protein produced by the organism or an antibody, such as a monoclonal antibody, specific to the organism. Exemplary biosensors adapted to detect proteolytic enzymes are described in U.S. Pat. No. 5,607,567 and toxins in U.S. Pat. Nos. 5,496,452; 5,521,101; and 5,567,301.

Any of the sensors 60 of the present invention may comprise one or more "proactive sensors". This is especially useful in embodiments where the detection of the health and/or nutritional marker precedes the onset of clinically observable health symptoms. As used in this application, the term "proactive sensor" refers to a sensor that is capable of detecting changes or signals on the body of the individual (i.e., skin) or in bodily waste, i.e., inputs, that directly relate or, at a minimum, correlate to the occurrence of an impending or potential health or skin related event. Proactive sensors may respond to one or more specific inputs as described above.

A proactive sensor 60 may detect an impending event or detect a parameter that directly relates, or at a minimum correlates to the occurrence of an impending event, particularly a systemic or skin health event (i.e., the presentation of clinically observable indications or symptoms). An impending event that may be detected or predicted by a proactive sensor 60 of the present invention may include early stages of lead poisoning, early stages of malnutrition and/or vitamin deficiency caused by nutrient malabsorption, diarrheal disease, skin irritation or rash (including candidiasis), and/or other types of illness or medical conditions of the subject such as a parasitic infestation. The detected health and/or nutritional marker or biological analyte may be one or more steps removed from the actual presentation of clinical symptoms. For example, the sensor may detect potential precursors to the above conditions (e.g., fecal contamination of the skin that may precede the elicitation of stress proteins which may, in turn, precede clinically observable skin irritation). A parameter that correlates to an event is any measurable input, signal such as one or more of the potential inputs listed above, that correlates with the occurrence of the event within the frame of reference of the system (i.e., a signal caused by the waste or the subject). Proactive sensors 60 in an device may measure one or more different inputs in order to predict an event. For example, the proactive sensor 60 may monitor for *Candida albicans* in the feces and residual colonic bacteria on the skin (i.e., detecting residual contamination) both of which are signals that may precede skin irritation.

In biosensor embodiments wherein the bio-recognition element does not produce an easily visible signal (e.g., a color change), the sensor 60 may include a transducer in communication with the bio-recognition element in order to convert the physico chemical signal from the bio-recognition element into a usable signal to the subject, caretaker, or component of the device (e.g., and actuator). Exemplary transducers may include electrochemical transducers (including potentiometric, amperometric, and conductimetric transducers), optical transducers (including flourescence, bioluminesence, total internal reflective resonance, and surface plasmon resonance), thermal transducers, and acoustic transducers, as known in the art. A power source, such as a miniature 3 volt watch battery or printed thin film lithium battery, may be connected with the sensor 60 to provide any required power.

The effectiveness of the biosensors of the present invention may be measured with the Response Factor Test described in the Test Method section below. The Response Factor describes the ratio of the response of the biosensor when exposed to fecal test material compared to the response of the biosensor when exposed to physiological saline solution and is useful in assessing the sensitivity of the biosensor for biologically active analytes expected to be found preferentially in feces versus urine. The biosensors of the present invention preferably have a response factor of at least 2, 3, or 5, more preferably at least 10, and even more preferably at least 20 when exposed to fecal test material in aqueous solution or test urine having a concentration of 1 gram of fecal test material per 1 gram of physiological saline solution. (Physiological saline solution is used here to represent the background input signal which is present in most natural environments such as aqueous body fluids.) Such biosensors are able to clearly distinguish between the presence of fecal material and the presence of physiological saline solution with respect to a target biologically active analyte specific to feces.

One way to detect feces is to detect skatole, a substance commonly found in fecal material. It has been found that the skatole concentration in feces is about 180 microgram per gram of fecal material whereas the skatole level in urine has been found to be substantially lower. Skatole is generally a product of microbiological degradation that originates from the catabolism of tryptophane in the intestinal system.

In one preferred embodiment of a skatole detecting biosensor, the biosensor comprises genetically engineered microorganisms which assimilate skatole and or other substances. The assimilation of skatole specific substances can be measured, for example, via the oxygen consumption during the assimilation process. Microorganisms suitable for detecting skatole include *Acinetobacter baumannii* TO136 (FERM P-12891, Japanese patent publication JP05304947), and Bacillus Sp TO141(FREM P-12914, disclosed in Japanese patent publication JP05304948). Suitable biosensors including such microorganisms are commercially available for example from Institut flur Chemo- und Biosensorik of Münster, Germany, under the designation Mikrobielle Sensoren.

If microorganisms are incorporated into a biosensor, they may be immobilized in the biosensor by techniques known in the art such as entrapment, adsorption, crosslinking, encapsulation, covalent attachment, any combination thereof, or the like. Further, the immobilization can be carried out on many different substrates such as known the art. In certain preferred embodiments, the immobilization substrate may be selected from the group of polymer based materials, hydrogels, tissues, nonwoven materials, woven materials.

In certain embodiments, the sensor 60, including any biosensor embodiments, may comprise, be disposed on, or be operatively associated with a microchip, such as a silicon chip, MEMs (i.e., micro electromechanical system) device, or an integrated circuit. Microchip-based biosensors may be known as "biochips". Regardless of the type of sensor, the microchip may comprise a multiplicity of sensor components having similar or different sensitivities, kinetics, and/or target analytes (i.e., markers) in an array adapted to detect differing levels or combinations of said analyte(s). Further, each sensor in such an array may provide a different type of signal, including those types disclosed herein, and may be associated with different actuators and/or controllers. Also, each sensor in an array may operate independently or in association with (e.g., in parallel, combination, or series) any number of other sensors in the array.

Any of the sensors 60 of the present invention may be disposed in and/or operatively connected to any portion of a device that will be exposed to the input that the sensor is designed to detect. For the purposes of the present invention, the term "operatively connected" refers to a means of communication such that the sensor 60 may signal some portion of the device 20 when the sensor 60 detects an input. The sensor 60 may be separate from and operatively connected to another portion of the sensor 60, another sensor 60, an actuator, a controller or some other portion or component of the device 20. "Operatively connected" may, for example, include a means of communication such as an electrical connection via a conductive wire or member, via a transmitted signal such as radio frequency, infrared or another transmitted frequency communication. Alternatively, the sensor 60 may be operatively connected via a mechanical connection such as a pneumatic or a hydraulic connection The sensor 60 may be integral with the device 20, or may be installed by the caretaker or medical personnel. The sensor during the course of the analysis, may also become at least partially detached from the device and may be adhered to the individual's skin (i.e., the patient or subject). The sensor may be affixed, permanently or detachably (e.g., via a mechanical fastening system like Velcro™ or a water soluble adhesive) to a support structure, including adhesive tapes, cellulosic or synthetic webs, nonwoven highlofts, films, scrims, foams, and the like. Further, the sensor 60 may be completely contained within the device such as device 20 or may have a receiving portion located in the device such that it will come into contact with the desired input and another portion such as a transmitting portion located either in the device or outside the device. The sensor 60 may be external to the device 20 yet operatively connected to some portion of the device 20 such that the sensor 60 may detect an input external to the device 20 and provide a signal to a controller and/or an actuator. In some embodiments, the sensor may be separate from the device, e.g., separately applied to some portion of the subject via adhesive or other means as known in the art, and/or may have one or more components separate from the device.

The device may be durable, such that it is completely reusable, or may be partially disposable, containing at least one disposable element. For example, the device may comprise, or be used in conjunction with disposable components, elements, and/or articles, including disposal probes and/or probe covers, adhesive attachment means, carrier structures, power sources such as batteries, sensors or components thereof, and/or colorimetric or fluorescent test strips.

The device of the present invention, as described above, is adapted to detect health and/or nutritional markers in bodily waste, such as feces. The device, or component thereof, may be wearable. Wearable devices or components may include elastic and other belts, disposable or durable clothing, disposable absorbent articles such as diapers, disposable waste-receiving articles such as colostomy bags, catheters, artificial stomas, adhesive or releasably attachable strips such as bandages and diagnostic strips, adhesively attached devices, and other wearable items as known in the art. Additionally, the device, or a component thereof may be releasably affixed to any of the above wearable articles or any other carrier structure that may be attached to the subject or a wearable article. An adhesively attached wearable device is shown in FIG. 1. The embodiment of the device shown in FIG. 1 comprises three sensors adapted to detect the presence of three different analytes and a display which is adapted to provide an indication of the presence of the analytes. (However, any number of sensors capable of detecting any number of different analytes is possible.) The sensors and display are affixed to a carrier which is releasably attached to a subject's skin via an adhesive.

Figure 2:
FIG. 2 shows an alternate embodiment of the present invention.
Figure 3:
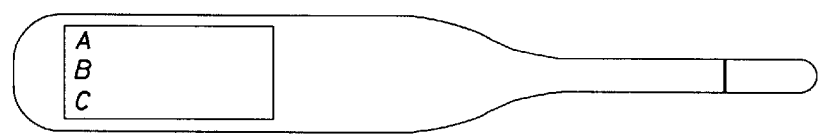
FIG. 3 shows an alternate embodiment of the present invention.

In alternative embodiments, the device may be a handheld unit similar in size and shape to handheld electronic oral thermometers, a non-limiting example of which is shown in FIG. 2. In this embodiment, a sensor, or sensing system, adapted to measure three different health and/or nutritional markers, is housed in one end of the device which is adapted for insertion into a body cavity or a waste sample. A display is disposed in the opposite end for convenient reading of the analysis of said markers. Depending on the type of sensor, i.e., especially optical sensors such as laser or LED sensors, a disposable probe cover 12 may be provided for hygienic use and easy cleaning. FIG. 3 shows a similar embodiment adapted for use without a disposable probe cover.

Figure 4:
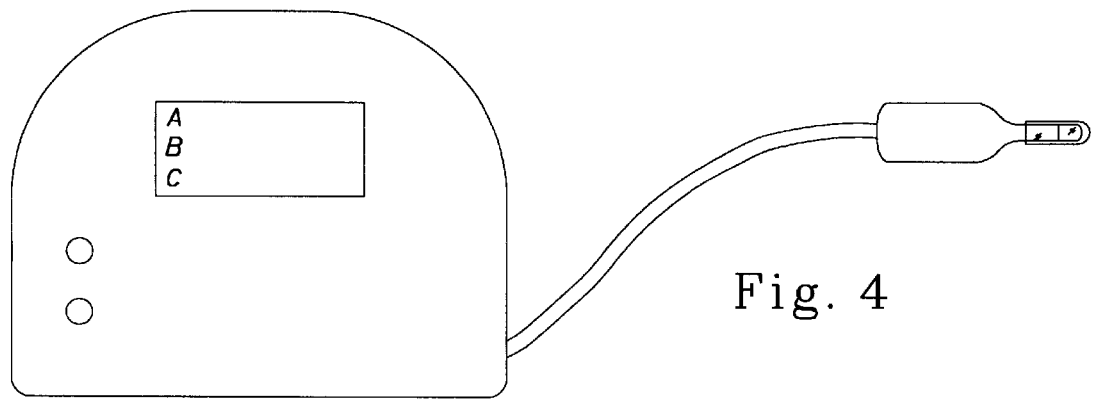
FIG. 4 shows an alternate embodiment of the present invention.

In alternate embodiments, the device may be a table or benchtop or portable unit, such as is depicted in FIG. 4. The device shown in FIG. 4 comprises a sensor or sensing system adapted to measure or detect one or more of three different health and/or nutritional markers in bodily waste, as described above. The device may comprise as sensor element containing the sensor(s) attached via a data cable to the main body of the device. Disposable probe covers 12 may be employed to provide hygienic use.

Power for the device is preferably electrical in nature, although other power sources, such as mechanical, chemical, or electrochemical are contemplated. Electrical power may be provided as DC current, such as from a disposable or rechargeable battery, or AC current, such as from a generator or wall outlet. Embodiments are contemplated wherein the device is powered or the battery is recharged via solar energy.

The signal provided by the device, or a component thereof, may be qualitative, such as an indication of the presence of a biological or chemical analyte, or quantitative, such as a concentration or relative amount, as described above. The output or signal may comprise a single signal, reading, or indication, or may comprise any number or combination of such outputs. The signal may be transient (i.e., in real time) or durable, such as a "peak" or "initial occurrence" reading.

Contact with the device or a component thereof may be passive or active. By "passive contact" is meant that the waste contacts at least a sensing portion of the device without any outside assistance by the caregiver or medical personnel. For example, passive contact may occur in embodiments wherein at least a portion of said device, such as a sensor, is adhesively affixed to the subjects skin in the perianal region prior to the application of a diaper. In this case, the sensor would contact the waste as a result of the normal defecation process. By "active contact" is meant that the subject, caregiver, or medical personnel may perform actions to bring about the contact of the waste and at least a sensing portion of the device. For example, waste/device contact is active in an embodiment wherein a probe or sensor is manually inserted into a previously collected waste sample.

In certain embodiments, the subject, caregiver, or medical personnel, may be required to take a sample, or aliquot, of the waste or treat the waste to be analyzed with a preparatory treatment, such as a buffer or sterilization, prior to testing with the device of this invention. The device may release, inject, or treat the waste, or a sample thereof, with a reagent, buffer, stabilizer, indicator, or other analysis aid as is known in the art.

In some embodiments, a wiping means or element may be provided to allow the caretaker or medical personnel to clean sufficient bodily waste from the sensor 60 to allow a visual assessment or reading of the signal (especially for sensor embodiments that provide such a signal). The wiping element may include a web (cellulosic or synthetic), nonwoven highloft, film, foam, rigid or semi-rigid squeegee like element, and the like disposed in the device and adapted such that the element may be used to clean the sensor display. The wiping element may be at least partially affixed the to a component of the device, such as a topsheet, in proximity to the sensor 60 by any known means in the art. The wiping means may optionally comprise water or any other known cleaning aid to facilitate cleaning of the subject or the sensor display.

In certain preferred embodiments, the device 20 also may comprise an actuator. As used in this application, the term "actuator" refers to a device that comprises "potential" and a means of transforming that potential to perform or activate a "responsive function." The potential of the actuator may comprise either stored or potential energy or stored material. The actuator thus may perform or activate a responsive function by transforming potential energy to kinetic energy or by releasing or delivering a stored material. A "responsive function" is defined for the purposes of the present invention as a function performed upon the bodily waste, the subject, the device, or a component or components thereof, or a signal to the subject or the caretaker. A component of bodily waste may include, for example, moisture, electrolytes, enzymes, volatile gases, bacteria, blood, etc. A component of the subject may also include skin, genitalia, the anus, the anal sphincter muscle, etc. Potential energy may be stored as mechanical, electrical, chemical or thermal energy. "Kinetic" energy as used in this application refers to the capacity to do work or to perform a responsive function as described above (e.g., expansion of a compressed device, rotation of a twisted device, a gel that moves as it changes phases, coating or treatment of skin or feces, inhibition of an enzyme, adjustment of pH, etc.).

The actuator of the present invention may release potential energy to perform or activate a responsive function upon the waste, the subject, the device, or a component thereof. The release of potential energy may transform mechanical, electrical, chemical or thermal potential energy into mechanical, electrical or chemical kinetic energy to perform the responsive function. Actuators may be triggered by a threshold level of an input to release potential energy to perform a responsive function or may respond continuously to an input as described below. For example, a compressed foam has stored compressive mechanical potential energy and may provide mechanical kinetic energy when it is released. A twisted foam has stored torsional mechanical potential energy that may provide mechanical kinetic energy, i.e., rotation, when it is released. In addition, stored chemical, electrical or thermal energy may be used to release electrical, mechanical, chemical or thermal kinetic energy. The actuator of a device, for example, may include one or more of the following: stored lotion, anti-fungal or antimicrobial agents, feces modification agents, enzyme inhibitors, pH buffers, dyes, pressurized gas, a compressed foam, a twisted foam, a pump, a closed system liquid transport member, an electrically sensitive gel, a pH sensitive gel, a salt concentration gel, etc. Potential energy may be stored in any manner sufficient to maintain or restrain it until it is required. Suitable means for maintaining and/or restraining such energy include batteries and/or capacitors, elastically, torsionally, compressively tensioned materials or structures in the form of unreacted reagents, and materials capable of performing physical or chemical functions (e.g., absorbents, emollients, pH buffers, enzyme inhibitors, feces modification agents; compressed gases, etc.).

Alternatively, the actuator of the present invention may comprise a quantity of a stored material that has the capacity to perform or activate a responsive function upon the waste, the subject, the device, or any component or components thereof In one embodiment, for example, the actuator may release or deliver a stored material that performs a responsive function. In this embodiment, the actuator may be triggered by a threshold level of an input to discontinuously release or deliver the stored material at a given time or may release or deliver the material continuously. The actuator may, for example, include stored lotion, skin care compositions, antifungal or antimicrobial agents, feces modification agents, enzyme inhibitors, pH buffers, dyes, etc. In certain preferred embodiments, the material may be delivered by an actuator such as an expanding resilient material, a released high pressure gas, etc.

Figure 7:
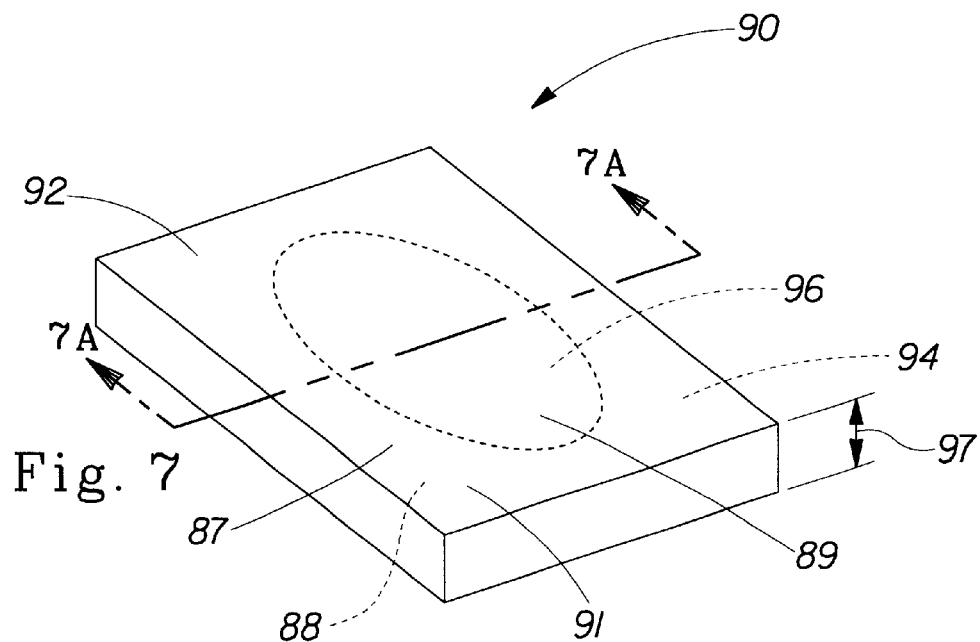
FIG. 7 shows a perspective view of a bodily waste isolation device of the present invention in a compressed state before activation.
Figure 7A:
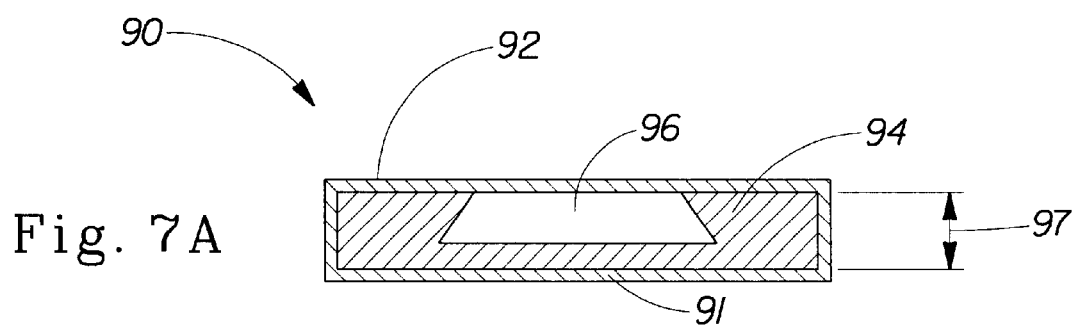
FIG. 7A shows a sectional view taken along line 7A—7A of FIG. 2.

FIGS. 7 and 7A illustrate an actuator 90 comprising a compressed resilient material 94, such as a foam, sealed under at least a partial vacuum within a pressure differentiation device 91. A pressure differentiation device, as used herein, is any device or structure that can maintain a resilient material in a compressed state (e.g., can store energy by providing a constraining pressure on the compressed resilient material 94). A "compressed state" is defined as the condition in which a material is maintained at a smaller volume than the material would have if unconstrained and under zero applied pressure. With respect to resilient materials, a compressed state may generally be achieved by applying a pressure to a surface of the material or via any other means known in the art. The pressure differentiation device may, for example, comprise a vacuum sealed bag or tensioned materials, such as elastic or inelastic bands or strands, strips, films, nonwoven, scrims, or foams, that constrain a resilient material. Preferably, the compression of the resilient material maintained by the pressure differentiation device 91 may be at least partially reduced (i.e., the compressed resilient material 94 may at least partially expand) via a trigger mechanism. A trigger mechanism is any element or device, such as a sensor, actuator, or combination thereof, that responds to an input to effect the equalization of pressure in the pressure differentiation device 91 and allow the compressed resilient material 94 to at least partially expand. Upon release of the compressed material, such as when a target biologically active analyte is detected, the compressed resilient material may expand and deliver the stored material. In some embodiments, it may be advantageous for the actuator to comprise a void space 96.

The resilient material may comprise any resilient material, including but not limited to, an EVA foam such as the ones available from Foamex Corporation of Eddystone, Pa. identified as SIF/210PP1 or Aquazone 80A foam, or from Sentinel Products Corporation of Hyannis, Mass. identified as MC1900 EVA 2 lb/ft$^3$, or a HIPE foam as described in U.S. Pat. No. 5,260,345 entitled "Absorbent Foam Materials For Aqueous Body Fluids and Absorbent Articles Containing Such Materials" issued to DesMarais et al. on Nov. 9, 1993; U.S. Pat. No. 5,387,207 entitled "Thin-Until-Wet Absorbent Foam Materials For Aqueous Body Fluids And Process For Making Same" issued to Dyer et al. on Feb. 7, 1995; and U.S. Pat. No. 5,625,222 entitled "Absorbent Foam Materials For Aqueous Fluids Made From high Internal Phase Emulsions Having Very High Water-To-Oil Ratios" issued to DesMarais et al. on Jul. 22, 1997. (Each of the patents identified above is incorporated by reference herein.)

In some embodiments of the present invention, the pressure differentiation device 91 may comprise a soluble bag. The soluble bag may be soluble in the presence of one or more different types of input, such as water, urine, fecal enzymes, a pH level, etc., and may have physical and/or chemical characteristics (e.g., thickness) that may be designed to set a threshold level of that input required to dissolve the bag. The soluble bag may, for example, comprise a plastic film that is soluble to water such as PVA films supplied by Chris-Craft Industrial Products, Inc. of South Holland, Ill. as MONOSOL M7031, M7030, M8630, M8534, or E6030 film, or H. B. Fuller Company of St. Paul, Minn. as HL 1636 or BL 1669-X. The film thickness, for example, may also be modified to provide a desired activation. The film used may, for example, also have a thickness in the range from about 0.0005 to about 0.0015 inches. An HL 1636 film having a thickness of about 0.001 inches, for example, will activate with a moisture content of about 0.049 grams per square inch.

The actuator may be disposed in and/or operatively connected to any portion of the device that will allow the actuator to perform a responsive function upon the bodily waste, the subject, the device, or a component thereof.

The device 20 may also include a controller. A "controller" is defined for the purposes of this application as a device that receives an input from a sensor and determines if one or more actions are to be taken. The controller may receive a signal from the sensor 60 and direct the actuator to perform a responsive function upon the bodily waste, the subject, the device or a component thereof Alternatively, the actuator may receive the signal directly from the sensor 60 and perform a responsive function upon the subject, the waste, the device or a component thereof. The controller may include materials that undergo chemical or physical change, may be a chemical, mechanical or electrical device that processes information from a sensor, etc. The biosensor 60 may comprise a transducer comprising a polylayer Langmuir-Blodgett film, at least a portion of which may function as a controller, wherein one or more layers includes a bio-recognition element. Upon contact with water, Langmuir-Blodgett films are known to spontaneously reorganize, resulting in regions with more layers than the original film and other regions having fewer layers. This reorganization may expose the bio-recognition element to the environment preferentially in the presence of water, such as in bodily waste, which may contain the target biological analyte. This may reduce false positives and/or extend the shelf-life of the biosensor. Alternatively, an electrical controller that receives signals such as electrical potential from an electrochemical sensor may receive and monitor multiple electrical signals and may repeatedly trigger the actuator. The controller may be integral with the sensor component, integral with the actuator component, or a separate component of the system.

The controller may be completely contained within the device such as device 20, may have a portion located in the device and a portion located outside the device, or may be located completely outside the device 20. The controller or a portion of a controller may be operatively connected to one or more sensors 60, one or more actuators 90, another portion of the controller or another portion of the device 20. The controller, for example, may receive a signal from the sensor 60 and provide a signal to the actuator, e.g., by a radio frequency (rf) transmission.

Although distinct structural elements may perform the sensor 60, actuator and controller functions, the sensor 60, actuator and/or controller functions of the present invention need not be performed by distinct structural elements. The sensor 60 and controller functions, for example, may be performed by the same structural element.

A "responsive system" is defined for the purposes of this application as a system that includes a sensor 60 and an actuator that acts upon the bodily waste, the subject, the device, or a component or components thereof when the sensor 60 detects the appropriate triggering input. Upon sensing a given input parameter, the actuator effects the release of stored energy or the release or delivery of stored material to perform a responsive function. For example, when a proactive sensor 60 including a transducer detects an impending event, the transducer provides a signal to the actuator effecting the release of stored energy. By detecting an input signal prior to the impending event, a responsive system in the device may be triggered to prepare for the event or to signal the caregiver or the subject of the impending event. This allows construction of devices in which the waste-management or treating technology is initially "hidden" or unobtrusive, but which is available at, or just before, the moment of need and/or in which the device may provide the caregiver or the subject the opportunity to prepare for an event in advance (e.g., administer a prohylactic treatment to the subject in the event of detected pathogenic microorganisms or residual fecal contamination). Regardless of the specific input, the sensor 60 in these embodiments may trigger an actuator to perform an action on the device, the subject or the environment to prepare for the occurrence of the event or provide a signal to the caregiver that the impending event is about to occur. If the sensor 60 comprises a sensing system, one actuator may be triggered by different sensors and/or signals, or different actuators may be triggered by different sensors and/or signals. Alternatively, one sensor and/or signal may trigger multiple actuators.

A responsive system may respond in either a "continuous" or a "discontinuous" manner. As used in this application, a "continuous responsive system" refers to a responsive system in which the output is quantitatively dependent upon the quantity of the input, i.e., continuously increasing quantities of the input are required to effect continuously increasing quantities of the output, or where the output of the responsive system comprises a passive release of a stored material. A super absorbent polymer placed in an absorbent core of an device, for example, provides a continuous response in which the output is quantitatively dependent upon the quantity of the input, i.e., as increasing quantities of liquid waste contact the super absorbent polymer, an increasing amount of the polymer contains that liquid until the capacity of the polymer is exhausted. A stoichiometric chemical reaction is another example of a system having a continuous response to increasing output. In the reaction A+excess B→C, for example, the amount of excess B converted to C is stoichiometrically and, therefore "continuously," related to the amount of A available in the system.

Figure 5A:
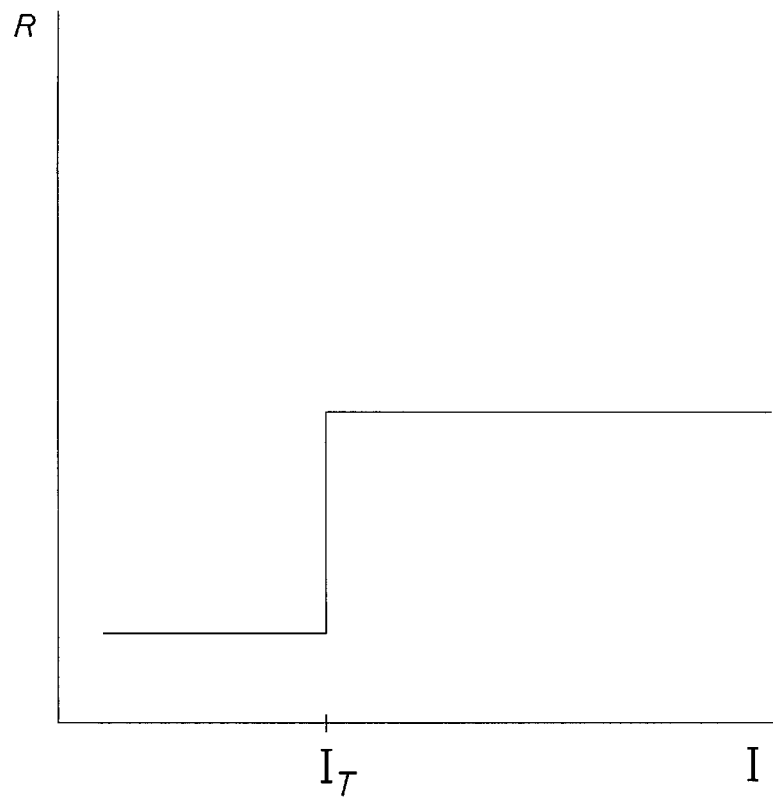
FIG. 5A shows an ideal output function of a discontinuous responsive system of the present invention having a single threshold level.

A "discontinuous responsive system" of the present invention, however, refers to a responsive system that has an output function that is essentially independent of the quantity of the input beyond a threshold level. For example, when one or more threshold levels of a given input are met, the responsive system may release all or a pre-designated portion of its stored energy or deliver, i.e., actively transport, all or a pre-designated portion of its stored material to perform a specific responsive function. In an ideal embodiment of the present invention, the output function, f(x), includes a "step" function as shown in FIG. 5A. In this embodiment, the rate of change in the output with increasing levels of input (d(output)/d(input)), i.e., the slope or first derivative f'(x) of the output function f(x), is preferably essentially zero when the amount of input is above or below the threshold level. At the threshold level, however, the d(output)/d(input) rate of change preferably approaches infinity. Thus, in the ideal discontinuous response, the limit of the function f(x−ϵ) as ϵ→0 is not equal to the limit of the function f(x+ϵ) as ϵ→0 i.e., lim f(x−ϵ)≠lim f(x+ϵ).

$\epsilon \to 0 \quad \epsilon \to 0$

Figure 6A:
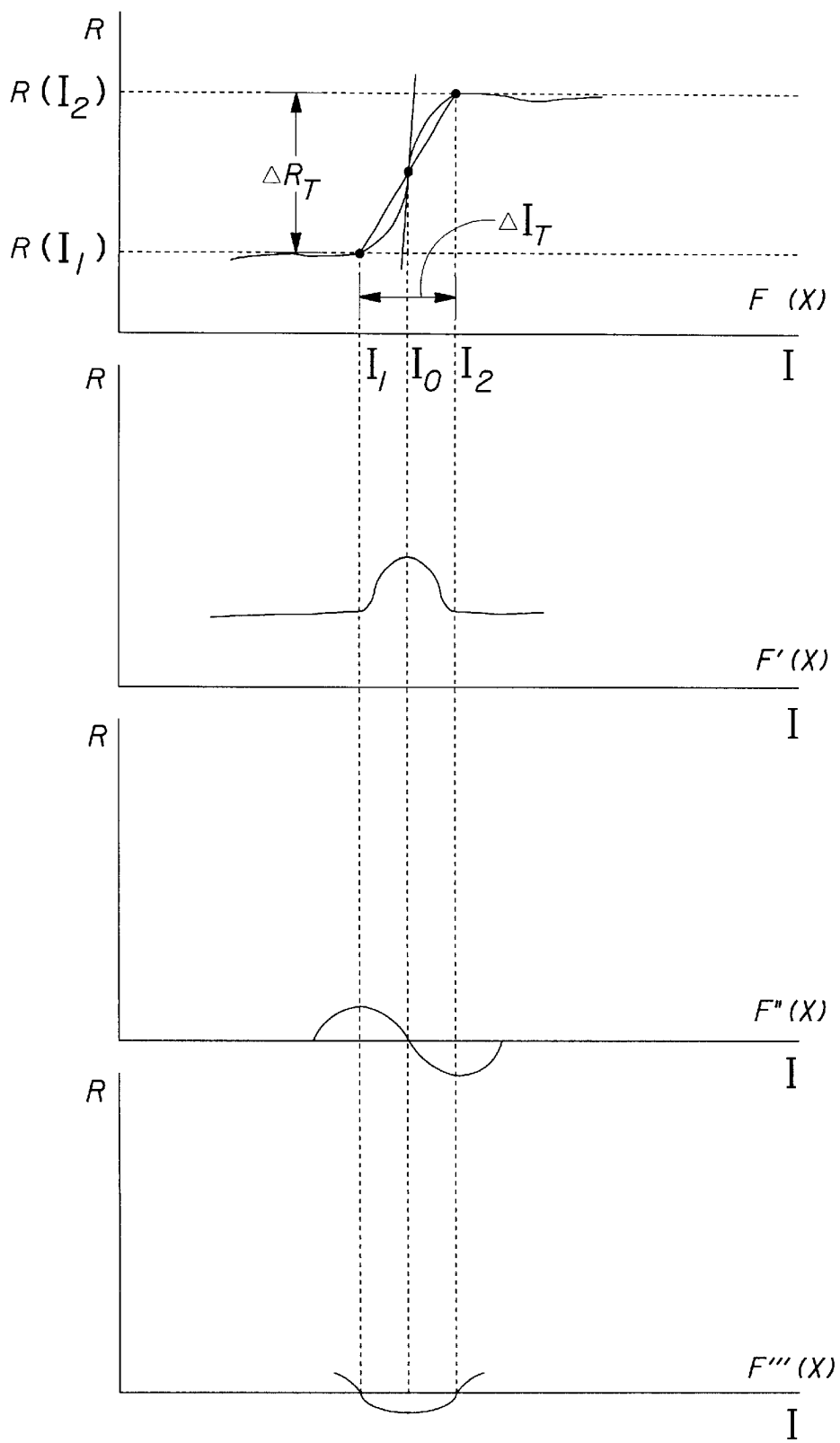
FIG. 6A shows an exemplary output function of a discontinuous responsive system of the present invention along with the first, second and third derivatives of the output function.

The present invention, however, recognizes that in the physical world an ideal instantaneous step change at the threshold level is not necessary and may not even be possible in many instances. In a preferred embodiment, it is only necessary that the output function have a virtual step change with very little change in the input at or around the threshold level of the input. Thus, the present invention contemplates a discontinuous responsive system of the present invention having an output function that responds in a sufficiently discontinuous manner in the transition region such that the output function has at least a minimum relative degree of steepness in the transition region. While not wishing to be limited to a particular method of describing or modeling a discontinuous system, in a preferred method of determining whether a given output function performs in a sufficiently discontinuous manner as defined for the purposes of the present invention, the slope of the output curve at the inflection point is compared with the relative slope of a line between the first and last points of the transition region. For example, FIG. 6A shows a graph of an exemplary output function, f(x) along with aligned graphs of the first, f'(x), and second, f"(x), and third, f'"(x), derivatives of the exemplary output function. The output function f(x) describes the effect of the in put (x or I) on the output or response (R(I)). For purposes of the present invention, the transition region is defined as the region between the relative maxima, R(I$_1$), and the minima, R(I$_2$), of the second derivative, f"(x), of the output function, f(x). The relative maxima, R(I$_1$), and the relative minima, R(I$_2$), are points at which the third derivative, f'"(x), equals zero. The inflection point, I$_0$, is defined as the point in the transition region at which the second derivative, f"(x), equals zero, i.e., $$\left. \frac{d^2 R}{dI^2} \right|_{I=I_0} = 0.$$

dI$^2$|I=I$_0$

The comparison of the slope of the output function at the inflection point to the slope of a line between the first and the last points of the transition region can be described by the equation:

$$\left. \frac{dR}{dI} \right|_{I=I_0} = k \frac{(\Delta R_T)}{(\Delta I_T)}.$$

dI|I=I$_0$ (ΔI$_T$)

In this equation dR/dI at the inflection point is the first derivative of the output function at that point. The term ΔI$_T$ is the change in the input to the responsive system between the first, I$_1$, and last, I$_2$, points of the transition region, i.e., I$_2$−I$_1$, and the term ΔR$_T$ is the change in the response of the output function between the first and last points of the transition region, i.e., R(I$_2$)−R(I$_1$). The coefficient k is a proportional constant that describes the relative steepness of the slope of the output function at the inflection point, I$_0$, compared to the slope of a line between the first and last points of the transition region. In order that the responsive system have a discontinuous output function, the proportional constant k must be at least about 2.0, preferably at least about 3.0, more preferably at least about 5.0, even more preferably at least about 10.0, with at least about 100.0 being the most preferred.

Figure 6B:
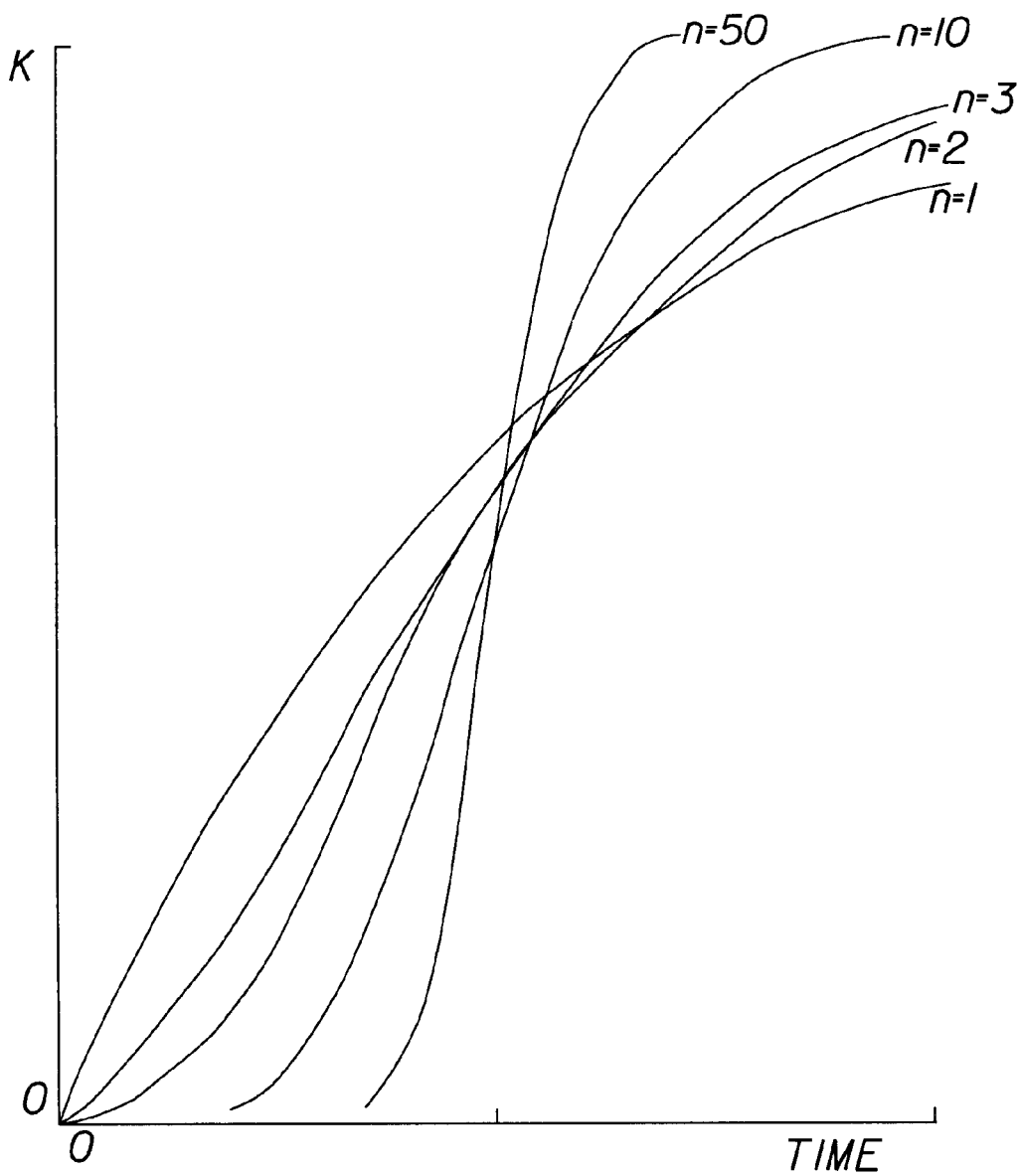
FIG. 6B shows a transfer function of a control system having a series of first order lags having an equal time constant.

In certain embodiments, the relative degree of steepness in the transition region of a discontinuous responsive system may also be modeled by a transfer function of a control system having a series of an integer number, n, first order lags with an equal time constant. The transfer function of the responsive system is defined for the purposes of the present invention as the ratio of the Laplace transforms of the output (responding variable) to the input (disturbing variable). See, e.g., Robert H. Perry & Don Green, *Perry's Chemical Engineers' Handbook*, Sixth Ed., Chap. 22 (McGraw Hill, Inc. 1984). As shown in FIG. 6B, the relative degree of steepness of an output function may be approximated by the formula: $KG(s)=K/(Ts+1)^n$ in which KG(s) is the transfer function, K is a proportional element, T is the time constant of the system, and n is the integer number of first order time lags. In this model, as the number n increases, the steepness of the output function in the transition region increases, and the model begins to approximate a discontinuous responsive system. Certain discontinuous responsive systems of the present invention preferably may be modeled by the above formula when n is greater than or equal to about 25, with n being greater than or equal to about 50 being more preferred, and n being greater than or equal to about 100 being the most preferred.

As shown in FIG. 5A, a responsive system of the present invention may include a single threshold level at which the responsive system may release all of its stored energy to perform a specific responsive function or may include multiple threshold levels at which the system may release a pre-designated portion of its stored energy to perform one or more specific responsive functions at each of the threshold levels. In an embodiment having a single threshold level, for example, the responsive system may release all of its stored energy to perform the entire responsive function when that threshold level is met. In such a single threshold embodiment, In this example, the discontinuous responsive system includes a system that has two states such as on or off. When a threshold quantity of an input such as a target biological material is present in the absorbent device, the responsive system may perform a single responsive function upon the waste, the subject, the device or a component thereof, such as providing an easily detectable visual signal to the subject or caregiver. Thus, the discontinuous responsive system may perform a one-time "switch-like" function that changes from one state to another in the presence of a threshold level of an input.

Figure 5B:
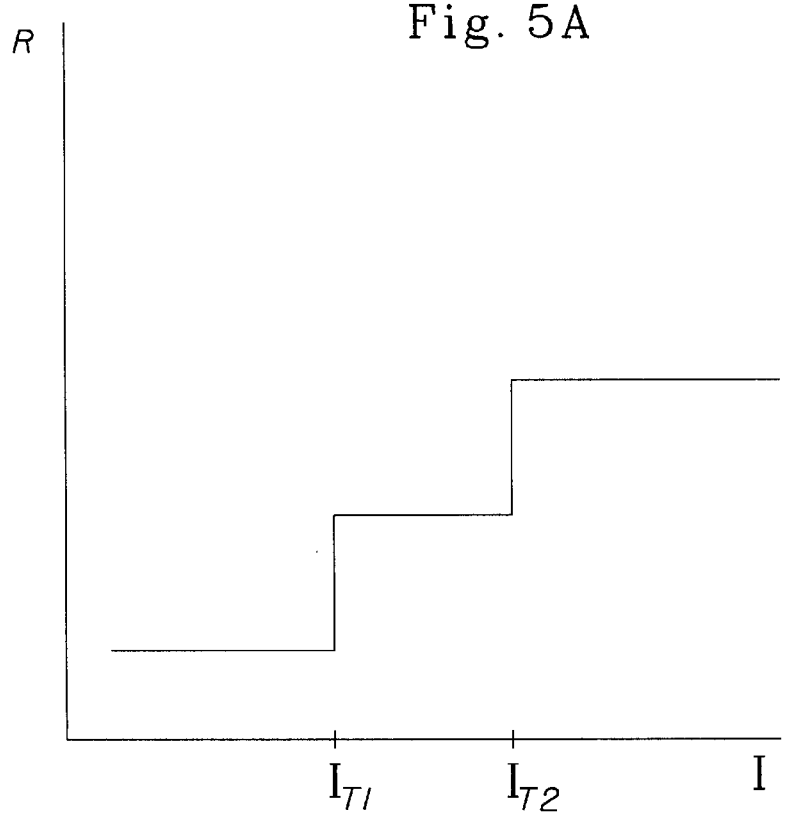
FIG. 5B shows an ideal output function of a discontinuous responsive system of the present invention having multiple threshold levels.

Alternatively, as shown in FIG. 5B, the responsive system may have multiple threshold levels at which when each threshold level is met the system may release a given "quanta" of energy or deliver a given quantity of material to perform a specific responsive function. In this embodiment, when each threshold level is met, a portion of the entire responsive function may be performed and/or different independent responsive functions may be performed in response to different threshold levels being met. In each transition region, the responsive system responds essentially the same as the transition region in the single threshold embodiment described above.

In addition, a responsive system may monitor multiple inputs such as one or more pathogenic bacteria and/or one or more fecal enzymes and perform one or more responsive functions when the threshold levels of the different inputs are met or may perform one responsive function only when two or more of the threshold levels of the different inputs are met. Thus, a controller may monitor multiple different inputs and perform a different responsive function when the threshold level of the different inputs are met. Alternatively, the controller may perform a logic OR-gate type function such that a responsive function may be performed when one or more threshold levels of the multiple inputs are met. The controller may also perform a logic AND-gate type function such that a responsive function may be performed when each threshold level of two or more different inputs is met.

The responsive system may also comprise a "closed loop" or an "open loop" system. A "closed loop" system, which is also referred to as a "feedback control loop" system, includes distinct sensor 60 and actuator components and performs a responsive function upon the input. In some preferred embodiments, the system may also use a detection or a measurement of an element or a parameter of the output condition as at least one trigger of the responsive function that is performed upon the input. The output condition may be the state of the input condition after the actuator has had the opportunity to perform a responsive function on the input condition. The responsive function may be performed when the output condition reaches a threshold level, or may be performed only when the output condition and one or more other conditions are met. Acting upon the input may include acting upon the element sensed, e.g., sensing a microorganism and acting upon the microorganism, or may include acting upon a composition of which the element sensed is an integral component, e.g., sensing a fecal bacteria and acting upon the fecal mass or residual feces on the subject's skin. As described above, a feedback control loop system includes at least two distinct components: the sensor 60 and the actuator. The sensor 60 detects an event, or a parameter associated with that event. The actuator receives a signal and performs a responsive function on the input condition detected by the sensor 60. The feedback control loop may further include a controller. In this case, the sensor 60 may provide a signal to the controller, and the controller may direct the actuator to perform a responsive function upon the input condition. The controller may be a separate component of the responsive system or the controller function may be performed by the sensor 60 and/or the actuator.

The feedback control loop may be "non-modulating" or "modulating." In a "non-modulating" feedback control loop responsive system the responsive system acts as a one-time switch in which the actuator performs a responsive function on the input when the threshold level of the output condition is met. For example, the sensor 60 may detect the presence of or measure the concentration of a specific pathogenic microorganism, and the actuator may signal the caretaker of a potential incipient infection. In this example, the actuator acts upon the input detected by the sensor 60. A "modulating" feedback control loop, however, includes a sensor 60, an actuator and a controller. In a modulating feedback control loop, the output condition is monitored constantly or repeatedly, and the controller directs the actuator to perform a responsive function on the input in order to maintain the output condition at a desired set point or within a desired range or to provide a continuous measurement of the level or concentration of the target biological analyte.

An "open loop" system, however, is a system that responds to the input to perform a responsive function without using feedback, i.e., the output has no effect upon the sensed input entering the system. An open loop system may include a responsive system that has a single device that performs the functions of both the sensor 60 and the actuator or may have distinct sensor 60 and actuator components in which the actuator acts upon something other than the input. Alternatively, an open loop responsive system may include a sensor 60 that detects bodily waste or a component of that bodily waste, and an actuator that performs a responsive function in a continuous or a discontinuous manner on something other than the input detected by the sensor 60.

Test Method

Response Factor Test:

With the Response Factor Test as described hereafter the response of a quantitative sensor as a reaction to exposure to a specific substance or composition can be measured.

The specific substances or compositions for which this test is suitable are:

fecal test material in aqueous solution having a concentration of 1 gram of fecal test material per 1 gram of physiological saline solution;

fecal test material in test urine solution having a concentration of 1 gram of fecal material per 1 gram of test urine solution;

test urine solution;

a solution of skatole in physiological saline solution having a concentration of 180 micrograms of skatole per gram of physiological saline solution; and physiological saline solution.

All measurements are carried at body temperature (37° Celsius). The method includes the following steps in the following order:

1) Record quantitative response of sensor after exposition to physiological saline solution for 24 hours. The background response is the maximum recorded response.

2) Expose sensor to specified substance or composition.

3) Record quantitative response of sensor while sensor is still exposed to the specified substance or composition for 24 hours. Substance response is the maximum recorded response.

The Response Factor is obtained by normalizing the substance response with the background response. In case, the thus obtained Response Factor is smaller than 1, the reciprocal value of the Response Factor is reported as the Response Factor.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention.

What is claimed is:

1. A device comprising:
   a microchip operatively associated with a sensor adapted to detect health markers in feces, the sensor further comprising a biosensor having a bio-recognition element and wherein the sensor is chemical, electrochemical, biochemical, or biological.

2. The device of claim 1 wherein the sensor provides a signal to the subject, caregiver, or an actuator.

3. The device of claim 2 wherein the signal is a visible indication.

4. The device of claim 2 wherein the signal is qualitative or quantitative.

5. The device of claim 2 wherein the signal is durable throughout at least the usage life of the device.

6. The device of claim 1 wherein the health marker is selected from the group of: heavy metals, radioactive substances, fats, enzymes, endogenous secretions, proteinaceous matter, mucous and microorganisms.

7. The device of claim 6 wherein the heavy metals are lead or mercury.

8. The device of claim 1 wherein the sensor detects the target health marker associated with a health condition prior to the onset of clinically observable symptoms of the condition.

9. The device of claim 1 wherein the sensor detects the health marker only above a pre-defined threshold level.

10. The device of claim 1 wherein the sensor additionally comprises a transducer.

11. The device of claim 10 wherein the transducer is selected from the group including electrochemical, optical, thermal, and acoustic transducers.

12. The device of claim 1 wherein the device additionally comprises a disposable probe cover.

13. The device of claim 1 wherein the sensor is affixed to a support element.

14. The device of claim 13 wherein the support element is an adhesive tape.

15. The device of claim 1 wherein the microchip comprises an array of sensors.

16. The device of claim 1 wherein the device includes a controller and wherein the sensor is detachable from the device.

17. The device of claim 1 wherein the sensor may be adhered to a wearer's skin.

18. The device of claim 1 further comprising an actuator that performs a responsive function when the sensor detects the health marker.

19. The device of claim 18 wherein the actuator transforms a potential energy to perform the responsive function, the potential energy being one or more selected from the group of mechanical energy, electrical energy, chemical energy.

20. The device of claim 1 wherein at least a portion of the device is capable of being worn by a wearer.

21. The device of claim 1 wherein the device is handheld.

22. The device of claim 1 wherein the device is powered by electrical power.

23. The device of claim 1 wherein the device treats the waste with a material selected from the group including: a reagent, a buffer, an indicator.

24. The device of claim 1 wherein the device comprises a laser diode sensor.

25. A device comprising a sensor adapted to detect nutritional markers and health markers in bodily waste or on human skin, the sensor further comprising a biosensor having a bio-recognition element and wherein the sensor is chemical, electrochemical, biochemical, or biological.

* * * * *